United States Patent [19]
Eivindson

[11] Patent Number: 5,644,401
[45] Date of Patent: Jul. 1, 1997

[54] METHOD FOR DIRECT CHEMICAL ANALYSIS OF MOLTEN METAL USING SPECTROMETER

[75] Inventor: Torkild Eivindson, Vennesla, Norway

[73] Assignee: Elkem A/S, Norway

[21] Appl. No.: 569,190

[22] PCT Filed: Jun. 21, 1994

[86] PCT No.: PCT/NO94/00114

§ 371 Date: Dec. 29, 1995

§ 102(e) Date: Dec. 29, 1995

[87] PCT Pub. No.: WO95/03546

PCT Pub. Date: Feb. 2, 1995

[30] Foreign Application Priority Data

Jul. 26, 1993 [NO] Norway ..................... 932682

[51] Int. Cl.$^6$ ........................................ G01N 21/31
[52] U.S. Cl. ................................................... 356/437
[58] Field of Search ............................. 356/382, 437

[56] References Cited

U.S. PATENT DOCUMENTS 5,106,413  4/1992  Takehawa ..................... 106/1.22

FOREIGN PATENT DOCUMENTS

| 0135375 | 3/1985 | European Pat. Off. . |
| 0402696 | 12/1990 | European Pat. Off. . |
| 2138540 | 2/1973 | Germany . |
| 2424689 | 3/1975 | Germany . |
| 0914112 | 12/1991 | Norway . |
| 2245058 | 12/1991 | United Kingdom ............ 356/437 |
| 9013008 | 11/1990 | WIPO . |

OTHER PUBLICATIONS

E. Nonomura et al., Transactions ISIJ, vol. 25, 1985 Direct Analysis of Silicon in Hot Metal by Emission Spectrometry.
K. Tsunoyama et al., Transactions ISIJ vol. 25, 1985 Direct Analysis of Molten Metal by Laser Emission Spectrometry.
M. Saeki, Processing from CETAS meeting in Luxemburg May 12–14, 1987 Direct Analysis of Liquid Metal.
G. Jecko, Proceeding of CETAS meeting in Luxemburg, May 12–14, 1987 L'Analyse Sur Metal Liquide Pourquoi?.
A. Golloch, Proceedings of CETAS meeting in Luxemburg, May 12–14 1987 Untersuchungen zur direkten Analyse von flussigem Stahl.
I.A. Majorov, et al., Spectrochimica Acta, vol. 36, No. 12, 1981, pp. 1223–1231 An atomic absorption method for continuous analytical monitoring of metal and alloy refining processes.

Primary Examiner—Vincent P. McGraw
Attorney, Agent, or Firm—Bierman, Muserlian and Lucas

[57] ABSTRACT

The invention relates to a method for quantitative analysis of one or more elements in a molten metal bath. Light from one or more light sources are focused against the surface of the molten bath and is reflected from the surface of the metal bath to a monochromator or a polychromator connected to detectors for detecting absorbed light in a gas layer associated with the melt of a wavelength or wavelengths corresponding to the element or elements to be analyzed. The absorption signals are proportional to the atom- or molecular density of the components to be analyzed and a function of the thickness of the gas layer and the concentration of the element or elements in the molten metal bath. The concentration of the elements to be analyzed is the calculated based or known relations between absorption signal, the thickness of the gas layer and the temperature of the metal bath.

4 Claims, 2 Drawing Sheets

METHOD FOR DIRECT CHEMICAL ANALYSIS OF MOLTEN METAL USING SPECTROMETER

TECHNICAL FIELD

The present invention relates to a method for direct chemical analysis of molten metal.

BACKGROUND ART

For many years it has been tried to develop methods for rapid chemical analysis of molten metal, especially in the steel industry. The driving force in this work has been the substantial economical savings which are possible by faster smelting- and refining processes and the possibility for an improved process control, thereby obtaining metals and metal alloys having a chemical composition within specifications.

The main type of rapid chemical analysis in the metal industry, especially in the steel industry, is being done by arc discharge optical emission spectrometry and x-ray fluorescence analysis on solid test specimens. The time interval from drawing a sample until a final analysis is obtained is normally in the range from 2 to 10 minutes.

A number of methods for direct analysis of molten metals have been proposed. Most of these methods are, however, difficult to use under operating conditions in metal smelting plants.

A group of proposed methods for direct analysis of molten metals is based on optical emission spectrometry. Thus use of arc discharge optical emission spectrometry on molten metal is described by Eizo Nonomura et al. in Transactions ISIJ, Vol. 25, 1985. Tests have shown that it is possible to use this principle for analysis of molten metal under controlled conditions, but that it is difficult to use under operating condition in smelting plants.

Laser-induced optical emission spectrometry for direct analysis of molten metals is described by Kouzou Tsunoyama et al. in Transactions ISIJ Vol. 25, 1985. By this method a laser is used for discharging the specimen, Masao Saeki, Proceeding from CETAS meeting in Luxemburg May 12.–14., 1987 has proposed to analyse the manganese content in a steel melt in a steel converter by using oxygen induced optical emission spectrometry.

Another method for direct analysis of molten metal comprises production of a volatized test specimen and transport of the specimen through a piping system to an IPC torch (Inductively coupled Plasma), wherein the test specimens is analysed. The test specimen can be obtained by a number of techniques, such as inserting a probe down into the metal bath and bubbling an inert gas through the bath, by reacting an oxidizing gas such as HCl, $O_2$ or $Cl_2$ with the bath, or by discharging an electric arc against the surface of the metal bath. Except for laboratory—and pilot plant tests, the method has not found any use. The method is described by G. Jecko and A. Golloch in Proceeding from CETAS meeting in Luxemburg May 12.–14., 1987.

Finally, I. A. Majorov et al, Spectrochimica Acta, Vol. 36, No. 12, 1981, page 1223–1231, has shown that atomic absorption spectrometry (AAS) can be used for continuous analysis of a metal melt during vacuum refining. In this method a light beam is passed through the gas phase above the molten metal bath in parallel with the surface of the molten metal bath.

For some elements and gases it is possible to analyse the content of the elements in a molten metal by using electrochemical sensors. Such electrochemical sensors can, however, only be used for analysing one element at a time and a sensor can only be used once. Electrochemical sensors are widely used for analysing oxygen content in steel melts and there are also described electrochemical sensors for analysing hydrogen, silicon, aluminium and calcium in molten metals.

DISCLOSURE OF INVENTION

It is an object of the present invention to provide a method for analysing the chemical composition of molten metals, which method gives a rapid and accurate analysis of the chemical composition of the molten metal and which method can be used during normal conditions in smelting plants.

Accordingly, the present invention relates to a method for quantitative analysis of one or more elements in a molten metal bath, wherein light beams from one or more light sources are focused against the surface of the metal bath, whereafter the light is reflected from the surface of the molten metal bath to a monochromator or a polychromator connected to suitable detectors for detecting absorbed light in a gas layer associated with the melt of a wavelength or wavelengths corresponding to the element or elements to be analyzed, which absorption signal or signals are proportional to the atomic or molecular density for the gas component or components to be analysed and a function of the thickness of the gas layer, whereafter the concentration of the element or the elements in the molten metal bath is calculated based on known relations between the absorption signal, the thickness of the gas layer and the temperature of the metal bath.

It is a basis for the present invention that any melt is associated with a gas layer above the melt which is in equilibrium with the melt. The composition of this gas layer is thus an indirect measure for the composition of the melt at a given temperature.

By using the surface of the metal bath as a reflector or mirror for the light, one can in a very simple way measure the absorption of light in the gas layer associated with the melt. It has surprisingly been found that even for molten metal baths having a flowing surface, good reflection of light is obtained, as the light beam projected against the surface of the metal bath can be focused on a very small area, virtually eliminating the effect of movements on the surface of the metal bath.

In order to obtain significant results, it is, however, necessary that at least the part of the surface of the metal bath on which the light beams am focused, is not covered by oxide layer, slag etc. Oxide layers and slag will also prevent the establishment of the gas-liquid equilibrium which is necessary in order to obtain correct results. For some melts it can thus be necessary to shield a part of the surface of the metal bath by using an open probe or the like and to supply inert gas to provide a clean metal surface on the part of the surface on which the light beam is being focused.

Disturbances in the form of dust particles, smoke and geometrical disturbances in the surface of the metal bath can be corrected by using known correction techniques, such as background correction using $D_2$-lamp, Smith Hieftje background correction and the Zeeman method.

The detection of absorbed light can be done either sequentially or simultaneously. By sequential detection, the absorption for one gas component is detected at a time. By simultaneous detection of absorbed light, the absorption for a number of components in the gas layer are detected simultaneously. By simultaneous analysis of absorbed light, the signal for one or more of the components in the gas can be used as an internal standard or for relative determination of the ratio between components in the molten metal bath.

If the measurements are made for a molten metal bath having one dominant element in a known amount, the absorption signal for this element in the gas layer above the melt can be used as an internal standard. The absorption signal from the internal standard can thus be used for corrections due to temperature changes and changes in the thickness of the gas layer.

The present invention will now be further described with reference to the accompanying drawings.

DETAILED DESCRIPTION OF PREFERRED EMBODIMENTS

Figure 1:
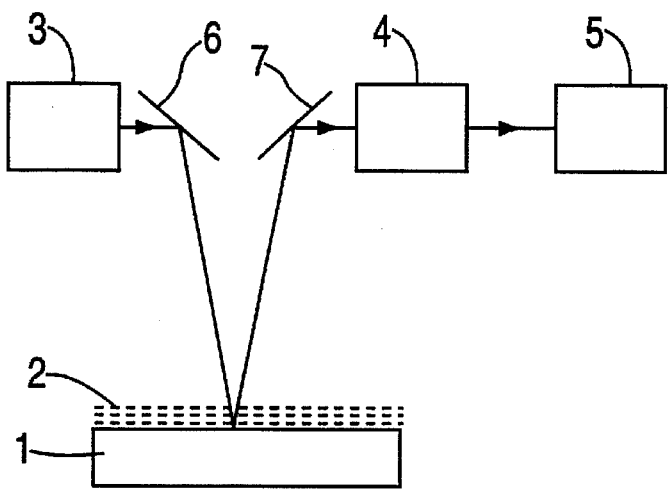
FIG. 1 shows an apparatus which can be used for carrying out the method of the present invention.

In FIG. 1 there is shown an apparatus which can be used in connection with the method of the present invention. On the figure there is shown a molten metal bath 1 having an associated gas layer 2 in equilibrium with the molten metal bath 1. The molten metal bath can be contained in any suitable container intended to contain a bath of molten metal, or can for example consist of metal flowing on a tapping spout of a smelting furnace or the like.

The apparatus for direct chemical analysis of the molten metal bath 1, comprises a light source 3, normally a hollow cathode lamp for emission of monochromatic light, a monochromator or polychromator 4 for selecting the actual wavelength for the element to be detected, a detector 5 for detecting light and lenses 6, 7 for focusing, guiding and catching the light beams. All units in the apparatus can be assembled in a housing and the apparatus can be connected to a computer for registration, treatment and storage of measured signals. Further, the apparatus can be connected to devices for displaying the measured results, such as a data screen or a printer.

By use of the apparatus shown in FIG. 1, a light beam is sent from the light source 3 and focused against the surface of the molten metal bath by mean of the lens 6. The light from the light source 3 comprises light having a wavelength corresponding to the resonance line or lines for the element or elements to be detected. The light beam passes through the gas layer 2 and is reflected from the surface of the molten metal bath 1 to the lens 7 and is directed to the monochromator or polychromator and to the detector 5. When passing through the gas layer 2 a part of the light having the wavelength for an absorption line for an actual atom, will be absorbed by atoms in the gas layer. The amount of absorption will be dependent on the atomic density of the actual metal atom in the gas layer and of the length of the path which the light passes in the gas layer 2. The absorption will be in accordance with Beer's law stating that the absorption is proportional to the concentration or the atomic density and the length of the path which the light passes through the absorption medium. As the gas layer associated with the surface of the molten metal bath approximately satisfies the requirements to an ideal gas, the atomic density for the actual element will be proportional to the partial pressure of the element and inversely proportional to the absolute temperature for the system. The partial pressure in the gas layer associated with a bath of molten metal is, according to Raoult's law, given as the concentration of that element in the melt for an ideal system and as the activity of the element in the melt for non-ideal system. The activity for an element in a molten metal bath is a function of the concentration of the element in the melt and of the temperature of the melt. The atomic absorption signal registered by the detector 5 will thus be a function of the chemical composition of the melt, the temperature of the melt and of the thickness of the gas layer 2 associated with the molten metal bath.

EXAMPLE 1

Figure 2:
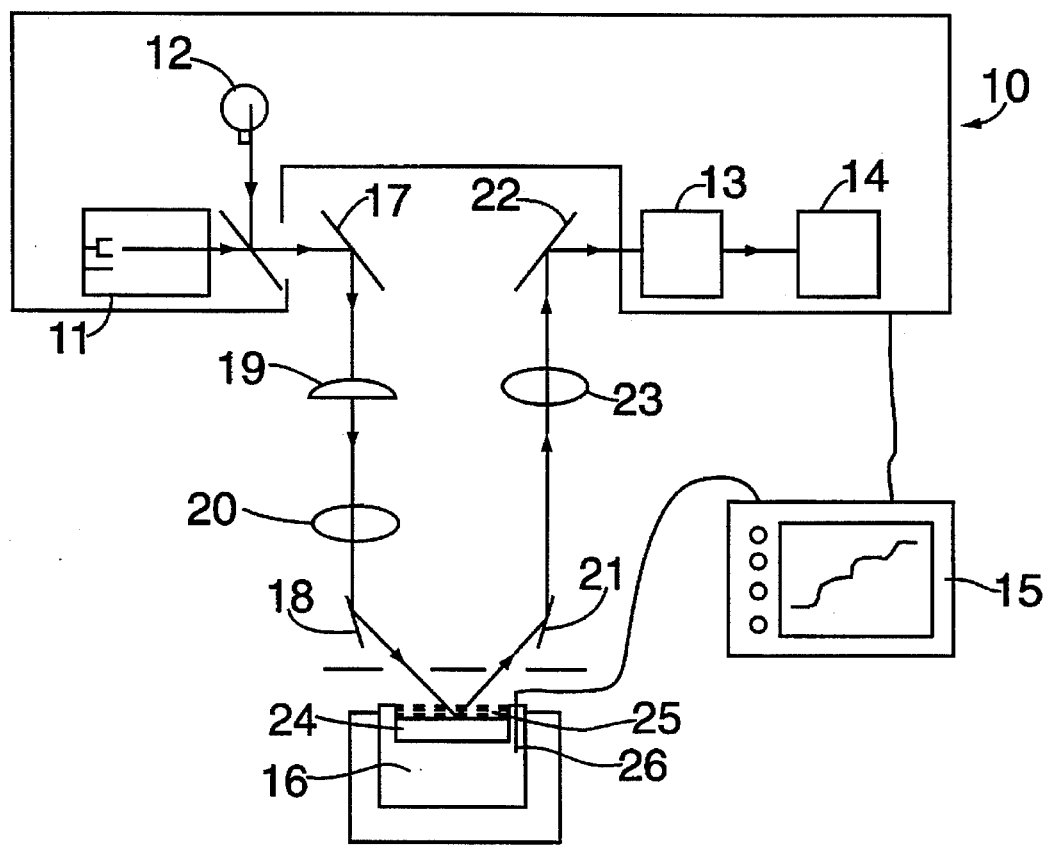
FIG. 2 shows an apparatus used in the example described below, and where.

An apparatus as shown in FIG. 2 was used to determine the correlation between defected atomic absorption signals for silver and the silver concentration in a copper-silver alloy.

The apparatus comprises a Perkin Elmer 303 atomic absorption spectrometer 10, having a hollow cathode lamp 11 with a $D_2$-lamp 12 for correction of background noise, a monochromator 13 and a detector 14. The detector 14 was connected to a printer 15.

About 100 grams of pure copper was melted in the resistance furnace 16. The light from the hollow cathode lamp 11 was thereafter focused against the surface of the copper melt 24 by means of mirrors 17, 18 and two UV lenses 19, 20. The light passed through the gas layer 25 and the light reflected from the surface of the copper melt was by the use of a mirror 21 and a lens 23 guided against the monochromator 23 of the AAS instrument. After having adjusted the mirrors and the lenses, the absorption signal for silver (328.1 nm) was adjusted to zero. Silver was thereafter added to the copper melt at intervals in mounts given in table 1. The temperature of the melt was during the test measured by a thermocouple 26.

TABLE 1

| Concentration | Measured absorbtion | |
|---|---|---|
| (ppm) | 328.1 nm | 338.3 nm |
| 1.3 | 0.000 | 0 |
| 23.6 | 0.087 | |
| 79.3 | 0.220 | |
| 244.8 | 0.626 | |
| 418.3 | 0.825 | 0.412 |
| 601.4 | | 0.533 |
| 803.2 | | 0.666 |
| 1060 | | 0.731 |
| 1380 | | 0.794 |

When the first silver was added to the copper melt an immediate increase in the absorption was recorded. At each addition of silver to the melt the absorption was registered for a period of two to three minutes. The absorption signal varied about a mean value with about ±0.05 absorbance units. It is not known if the observed variation in the detected absorbance is due to the AAS apparatus, non-optimal adjustment of mirrors and lenses or other effects. Silver was added in small amounts to the melt until the absorption (328.1 nm) reached about 0.800.

Figure 3:
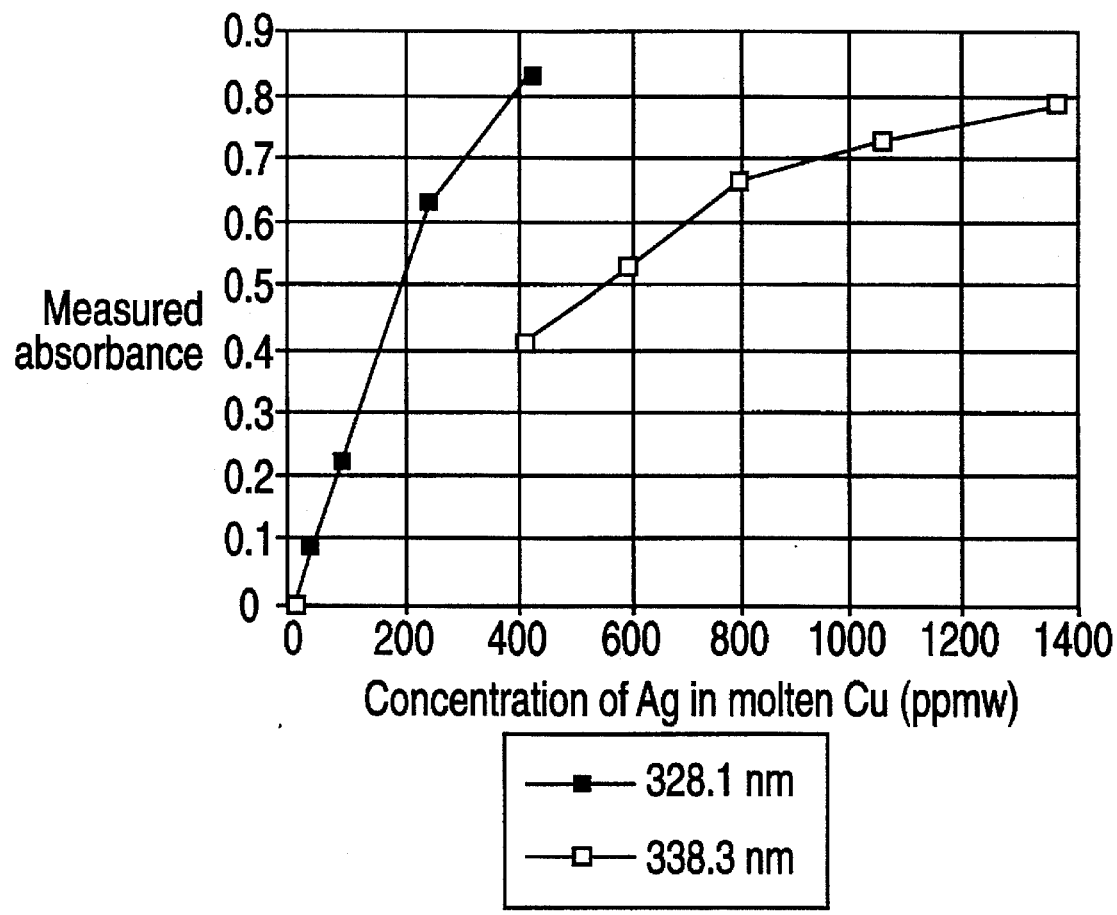
FIG. 3 shows a diagram for measured absorption as a function of the silver content in a copper-silver alloy.

The monochromator was thereafter adjusted to a less sensitive absorption line for silver (338.3 nm) and the absorption was detected. Additional silver was added to the melt and again the absorption was recorded for each addition. The temperature of the melt was kept constant during the test. When the test was finished the metal was weighed and the silver concentration in the copper was calculated. The measured absorption figures and the corresponding concentrations of silver are shown in table 1 and in FIG. 3.

The results show a good correlation between the recorded absorption figures and the concentration of silver in the melt. During the test no precautions were taken in order to maintain a defined gas layer above the melt. The test shows that the thickness of the gas layer is relatively constant.

I claim:

1. A method for quantitative analysis of one or more elements in a molten metal bath, characterized in that light beams from one or more light sources are focused against the surface of the metal bath, whereafter the light is reflected from the surface of the molten metal bath to a monochromator or a polychromator connected to suitable detectors for detecting absorbed light in a gas layer associated with and in equilibrium with the melt of a wavelength or wavelengths corresponding to the element or elements to be analyzed, which absorption signal or signals are proportional to the atom- or molecular density for the gas component or components to be analysed and a function of the thickness of the gas layer, whereafter the concentration of the element or the elements in the molten metal bath is calculated based on known relations between the absorption signals, the thickness of the gas layer and the temperature of the metal bath.

2. Method according to claim 1, characterized in that at least the part of the surface of the metal bath on which the light beam is focused, is shielded against formation of oxide layers and slag.

3. Method according to claim 2, characterized in that a part of the surface of the metal bath is shielded by using a probe.

4. Method according to claim 2, characterized in that an inert gas is supplied to the surface of the metal bath.

* * * * *